United States Patent
Lee et al.

(10) Patent No.: US 10,246,676 B2
(45) Date of Patent: Apr. 2, 2019

(54) CELL STIMULATION APPARATUS

(71) Applicant: INDUSTRY-ACADEMIC COOPERATION FOUNDATION, YONSEI UNIVERSITY, Seoul (KR)

(72) Inventors: Tae Yoon Lee, Seoul (KR); Hee Tak Han, Seoul (KR); Jung Mok Seo, Seoul (KR); Se Ra Shin, Seoul (KR); Hyun Chul Kim, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 173 days.

(21) Appl. No.: 15/414,031

(22) Filed: Jan. 24, 2017

(65) Prior Publication Data
US 2018/0112172 A1 Apr. 26, 2018

(30) Foreign Application Priority Data
Oct. 20, 2016 (KR) .................. 10-2016-0136464

(51) Int. Cl.
C12M 1/00 (2006.01)
C12M 1/26 (2006.01)
C12M 1/32 (2006.01)
C12M 1/42 (2006.01)

(52) U.S. Cl.
CPC ............ *C12M 33/04* (2013.01); *C12M 23/12* (2013.01); *C12M 23/26* (2013.01); *C12M 35/04* (2013.01)

(58) Field of Classification Search
CPC ...... C12M 23/26; C12M 35/04; C12M 23/12; C12M 33/04
See application file for complete search history.

(56) References Cited

U.S. PATENT DOCUMENTS 4,789,601 A * 12/1988 Banes ................... A61L 27/18
428/116
9,206,391 B2 * 12/2015 Hase .................... C12N 5/0062

FOREIGN PATENT DOCUMENTS

| KR | 10-0799988 B1 | 1/2008 |
| KR | 10-2010-0067298 A | 6/2010 |
| KR | 10-2011-0044226 A | 4/2011 |
| KR | 10-2015-0032126 A | 3/2015 |
| KR | 10-2015-0125350 A | 11/2015 |

* cited by examiner

*Primary Examiner* — Gautam Prakash
(74) *Attorney, Agent, or Firm* — Sughrue Mion, PLLC

(57) ABSTRACT

Disclosed is a cell stimulation apparatus. In particular, a cell stimulation apparatus according to an embodiment of the present disclosure includes a cell containment part in which at least one cell containment groove containing cells is formed; and a pressure control part that supports the cell containment part and transforms the at least one cell containment groove by applying pressure to the cell containment part, wherein a bottom of the at least one cell containment groove is made of a flexible material.

10 Claims, 8 Drawing Sheets

CELL STIMULATION APPARATUS

CROSS-REFERENCE TO RELATED APPLICATION

This application claims the priority benefit of Korean Patent Application No. 10-2016-0136464, filed on Oct. 20, 2016 in the Korean Intellectual Property Office, the disclosure of which is incorporated herein by reference.

BACKGROUND OF THE INVENTION

Field of the Invention

The present disclosure relates to a cell stimulation apparatus, and more particularly to a cell stimulation apparatus providing mechanical stimulation to cells using a pressure controller that enables application of vacuum pressure to a container bottom surface made of a flexible material and, at the same time, configured to culture cells therein.

Description of the Related Art

In the field of cell biology, research into cellular responses to various stimuli is very important in that important clues about cellular metabolism, such as protein expression, cell apoptosis, and cell differentiation, are provided at the gene level, and, through such research, the mechanisms of disease development can be understood and drug development can be accomplished.

In particular, since mechanical stimuli, such as tensile force, shear force, and compressive force, can be easily encountered in everyday life, research into cellular responses to mechanical stimulation has attracted great attention. Indeed, a previous report reported that repeated mechanical stimulation induces diseases, such as arthritis and keloids, and greatly affects the proliferation rate of stem cells and differentiation thereof into specific cells.

In connection with this, Korean Patent Laid-Open No. 10-2015-0125350 introduced a method of indirectly stimulating cells in a container structure using ultrasound. However, since this method uses indirect stimulation, there are limitations in quantifying stimulation applied to the cell, and the intensity of stimulation applied to cells varies depending on the composition and amount of a cell culture medium.

As another method, Korean Patent Laid-Open No. 10-2010-0067298 introduced a device for applying direct and mechanical stimulation by means of a manufactured micro-needle using a micro electro-mechanical system (MEMS). However, this device has a limitation in that only sting (ok?) stimulation is applied.

In addition, Korean Patent No. 10-0799988 introduced a cell culture apparatus configured to apply various mechanical stimuli to stem cell cultures and a method of culturing stem cells using the same. In particular, the device enables application of three stimuli: tensile, compression, and torsion. However, this device is constituted of a motor, a pump, scaffolds, and the like, thereby being complex and having inefficient spatial property. Accordingly, the device can be applied to only a small number of cells, whereby it is difficult to apply the same to real industrialization such as facilities for producing stem cell culture media.

RELATED DOCUMENTS

Patent Documents

Korean Patent Laid-Open No. 10-2015-0125350
Korean Patent Laid-Open No. 10-2010-0067298
Korean Patent No. 10-0799988

SUMMARY OF THE INVENTION

Therefore, the present invention has been made in view of the above problems, and it is an object of the present invention to provide a cell stimulation apparatus providing mechanical stimulation to cells using a pressure controller that enables application of vacuum pressure to a container bottom surface made of a flexible material and, at the same time, configured to culture cells therein.

In accordance with an aspect of the present invention, the above and other objects can be accomplished by the provision of a cell stimulation apparatus, including: a cell containment part in which at least one cell containment groove containing cells is formed; and a pressure control part that supports the cell containment part and transforms the at least one cell containment groove by applying pressure to the cell containment part, wherein a bottom of the at least one cell containment groove is made of a flexible material.

The bottom of the at least one cell containment groove may be made of a stretchable polymer material.

The at least one cell containment groove may be formed in a lattice shape in a plurality of rows and columns on the cell containment part, and the pressure control part may independently control pressure applied to each to the at least one cell containment groove.

A plurality of protrusions may be formed in the at least one cell containment groove.

The pressure control part may include a stage which supports the cell containment part and in which at least one air hole, through which air enters and exits, is formed; a pump that applies vacuum pressure to the cell containment part; and a control part that controls driving of the pump.

The at least one air hole may be formed at an upper part of the stage and at a position corresponding to the bottom of the at least one cell containment groove.

A plurality of air suction pipes may be provided to the stage, wherein the air suction pipes may be disposed at a position corresponding to the at least one cell containment groove, and the air suction pipes in each of rows or columns formed by the at least one cell containment groove may be independently controlled.

Cell containment grooves included in an identical row among rows formed by the at least one cell containment groove may be stretched together, and each row formed by the at least one cell containment groove may be separately controlled, the stage may include a communication pipe communicating between the air suction pipes, and the communication pipe may include valves for controlling entry and exit of air which is sucked through the air suction pipes by driving of the pump.

The valves may control flow of air such that air is sucked only through air suction pipes disposed at a desired row among the air suction pipes.

In accordance with another aspect of the present invention, there is provided a cell stimulation apparatus, including: a cell containment part in which at least one cell containment groove containing cells is formed; a protrusion part that is formed, in a concave and convex shape, on an inner circumferential surface of the at least one cell containment groove; and a pressure control part that supports the cell containment part and controls intensity of mechanical stimulation applied to cells by applying pressure to the cell containment part, wherein a bottom of the at least one cell containment groove is made of a flexible material.

The bottom and protrusion part of the at least one cell containment groove may be made of a stretchable polymer material.

The cell stimulation apparatus may include a stage which supports the cell containment part and in which at least one air hole, through which air enters and exits, is formed; a pump that applies vacuum pressure to the cell containment part; and a control part that controls driving of the pump.

A plurality of air suction pipes may be provided to the stage, wherein the air suction pipes may be disposed at a position corresponding to the at least one cell containment groove, and the air suction pipes in each of rows or columns formed by the at least one cell containment groove may be independently controlled.

Cell containment grooves included in an identical row among rows formed by the at least one cell containment groove may be stretched together, and each row formed by the at least one cell containment groove may be separately controlled, the stage may include a communication pipe communicating between the air suction pipes that are disposed per row formed by the at least one cell containment groove, and the communication pipe may include valves for controlling entry and exit of air which is sucked through the air suction pipes by driving of the pump.

The valves may control flow of air such that air is sucked only through air suction pipes disposed at a desired row among the air suction pipes.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF THE INVENTION

Hereinafter, the present invention will be described in detail by explaining particular embodiments of the invention with reference to the attached drawings. However, it should be understood that the spirit and scope of the present disclosure are not limited to the embodiments and can be modified by addition, modification, or deletion of elements constituting the embodiments and such additions, modifications, and deletions are also within the spirit and scope of the present disclosure.

Figure 1:
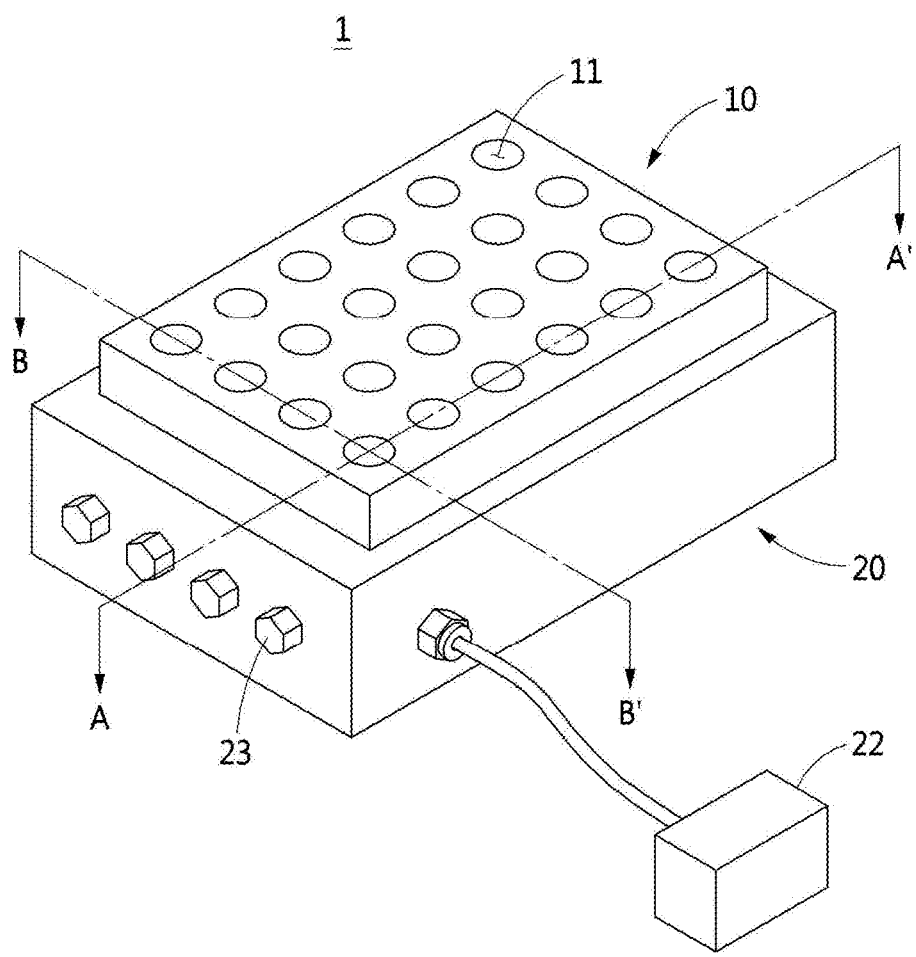
FIG. 1 illustrates a perspective view of a cell stimulation apparatus according to an embodiment of the present disclosure.
Figure 2A:
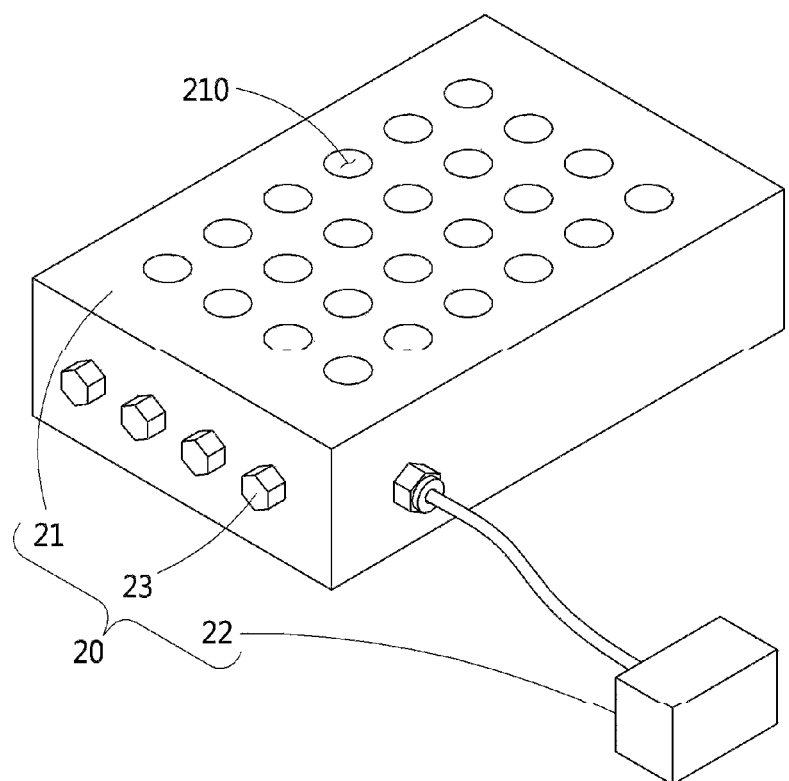
FIG. 2(a) illustrates a perspective view of a pressure control part of a cell stimulation apparatus according to an embodiment of the present disclosure.
Figure 2B:
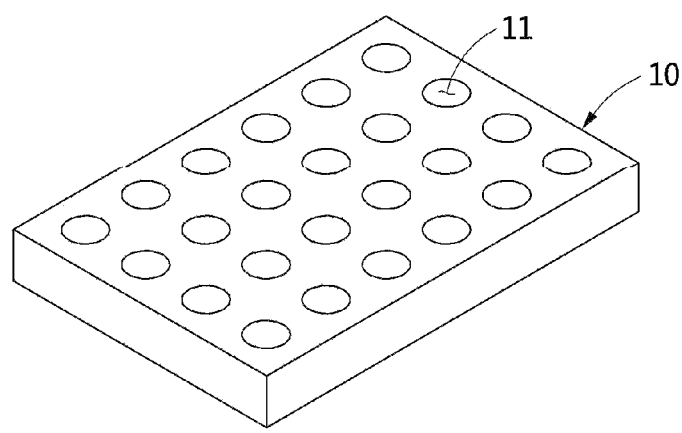
FIG. 2(b) illustrates a perspective view of a cell containment part of a cell stimulation apparatus according to an embodiment of the present disclosure.
Figure 3:
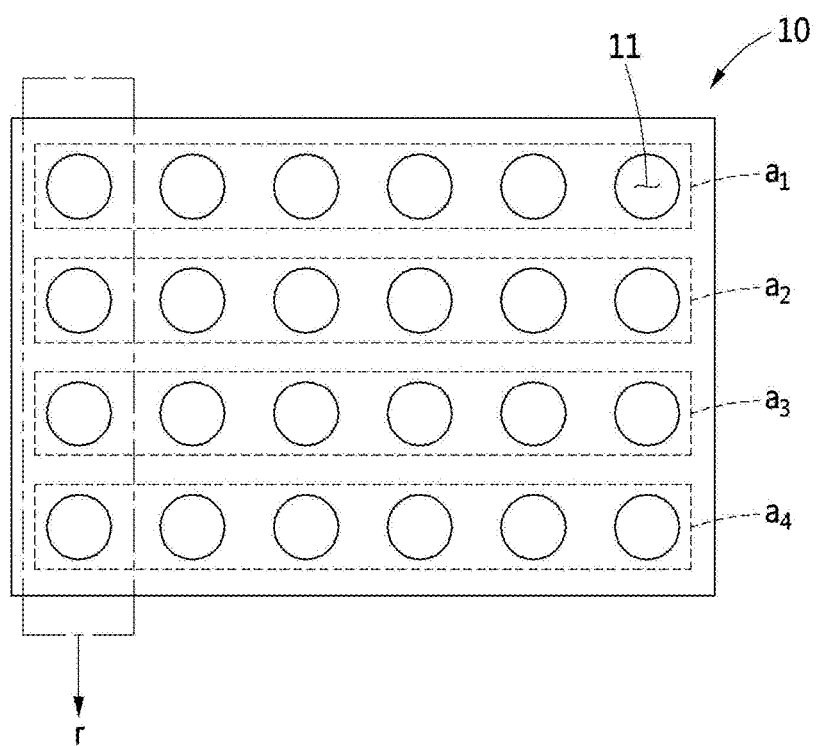
FIG. 3 illustrates a top plan view of the cell containment part of FIG. 2(b)
Figure 4A:
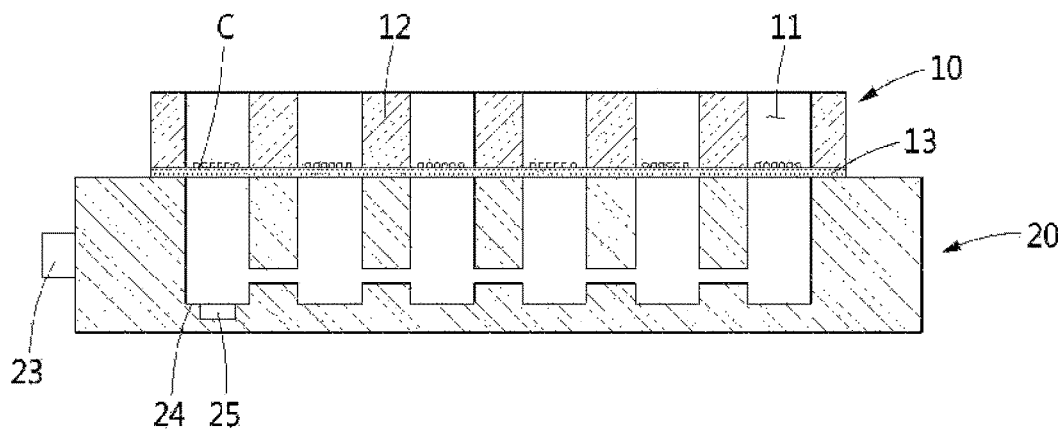
FIG. 4(a) illustrates a sectional view taken along A-A' line of FIG. 1.
Figure 4B:
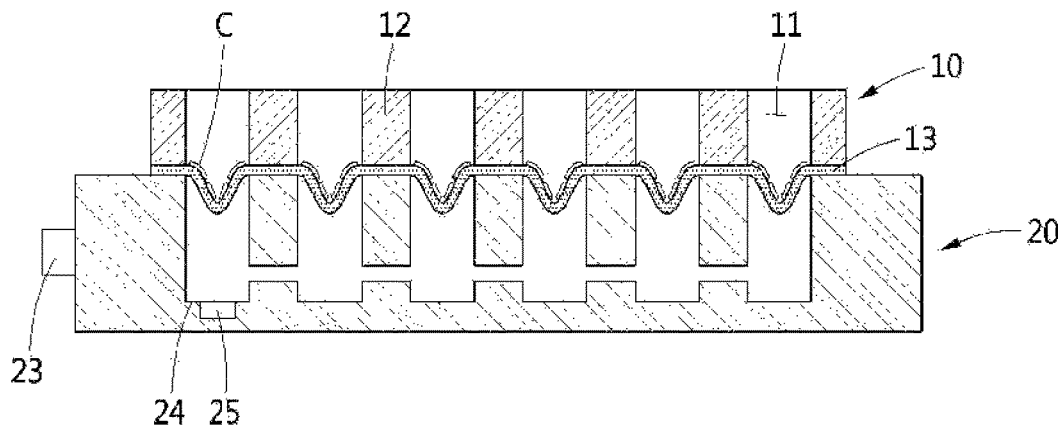
FIG. 4(b) schematically illustrates the shapes of cells elongated due to bottoms, which have been transformed by vacuum pressure, of a cell containment part of FIG. 4(a)
Figure 5A:
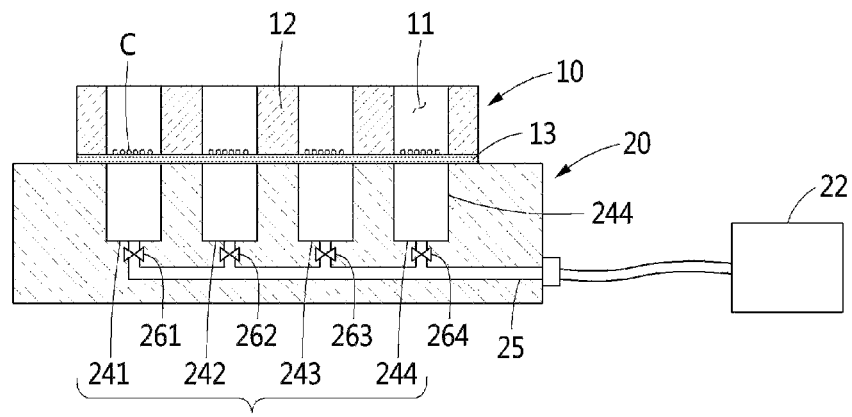
FIG. 5(a) illustrates a sectional view taken along B-B' line of FIG. 1.
Figure 5B:
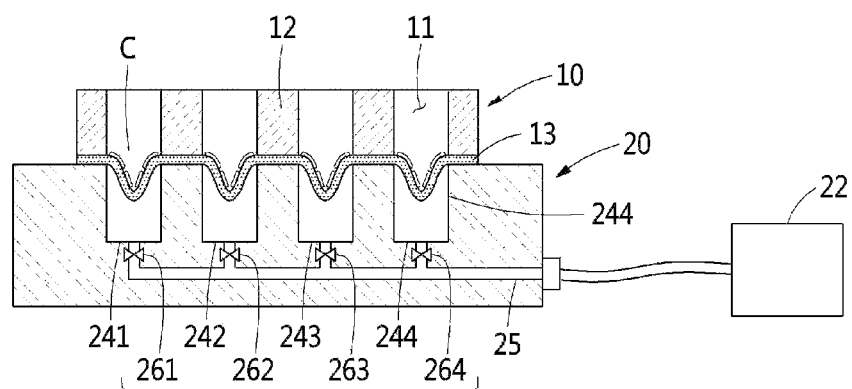
FIG. 5(b) schematically illustrates the shapes of cells elongated due to bottoms, which have been transformed by vacuum pressure, of a cell containment part of FIG. 5(a)
Figure 5C:
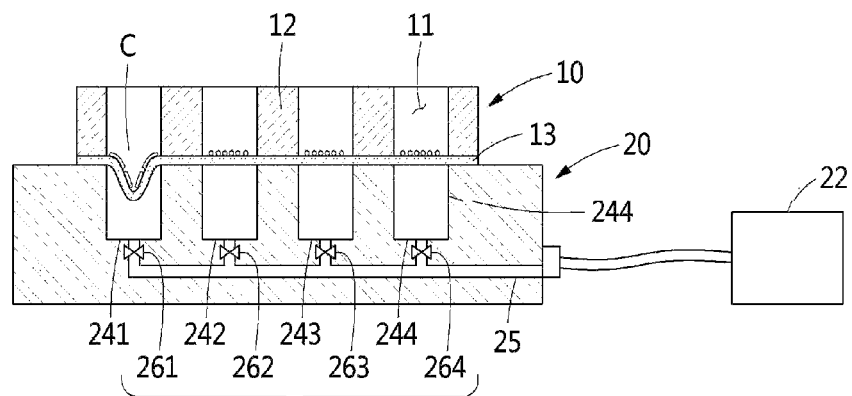
FIG. 5(c) schematically illustrates the shapes of cells elongated due to transformation of the bottom of a cell containment groove, which has been disposed in a predetermined column among the cell containment part of FIG. 5(a), by vacuum pressure.

FIG. 1 illustrates a perspective view of a cell stimulation apparatus according to an embodiment of the present disclosure, FIG. 2(a) illustrates a perspective view of a pressure control part of a cell stimulation apparatus according to an embodiment of the present disclosure, FIG. 2(b) illustrates a perspective view of a cell containment part of a cell stimulation apparatus according to an embodiment of the present disclosure, FIG. 3 illustrates a top plan view of the cell containment part of FIG. 2(b), FIG. 4(a) illustrates a sectional view taken along A-A' line of FIG. 1, FIG. 4(b) schematically illustrates the shapes of cells elongated due to bottoms, which have been transformed by vacuum pressure, of a cell containment part of FIG. 4(a), FIG. 5(a) illustrates a sectional view taken along B-B' line of FIG. 1, FIG. 5(b) schematically illustrates the shapes of cells elongated due to bottoms, which have been transformed by vacuum pressure, of a cell containment part of FIG. 5(a), and FIG. 5(c) schematically illustrates the shapes of cells elongated due to transformation of the bottom of a cell containment groove, which has been disposed in a predetermined column among the cell containment part of FIG. 5(a), by vacuum pressure.

Referring to FIG. 1 to FIG. 5, a cell stimulation apparatus 1 according to an embodiment of the present disclosure may include a cell containment part 10 and a pressure control part 20.

Cells C contained in the cell stimulation apparatus 1 according to the present disclosure may be, for examples, various cell types such as stem cells, skin cells, or neuron cells. Preferably, any cell types affected by mechanical stimulation are applied.

The cell containment part 10 may include a well plate in which a test sample, e.g., blood, bacteria, cells, etc., is contained to investigate or measure the state thereof. In addition, the cell containment part 10 may be manufactured to have various specifications according to user's requirements.

The cell containment part 10 may include a plurality of cell containment grooves 11 containing cells C, and may be made of a flexible material. For example, the inner circumferential surface 12 of the cell containment part 10 may be made of polyethylene terephthalate (PET), polystyrene (PS), polydimethylsiloxane (PDMS), silicon, or the like. Preferably, the inner circumferential surface 12 of the cell containment part 10 may be made of any material so long as cells can be suitably cultured and the shape of the cell containment part 10 can be maintained. In addition, a bottom surface 13 of the cell containment part 10 may be made of a stretchable polymer material such as polydimethylsiloxane (PDMS) or polyurethane (PU).

More preferably, since cells C, which are sensitive to the surrounding environment, do not grow on a cytotoxic material (e.g., silver), the cell containment part 10 for containing the cells C is made of a biocompatible material.

The cell containment grooves 11 may be formed to be arranged in a lattice shape in a plurality of rows and columns on the cell containment part 10. For example, a plurality of cell containment grooves 11 is formed in the cell containment part 10 and spaced from each other by a predetermined interval. The cell containment grooves 11 may be arranged in a plurality of rows ($a_1$, $a_2$, $a_3$, $a_4$). Pressure applied to the cell containment grooves 11 disposed in each row ($a_1$, $a_2$, $a_3$, $a_4$) may be independently controlled by the pressure control part 20 that is described below. In addition, each row ($a_1$, $a_2$, $a_3$, $a_4$) formed by the cell containment grooves 11 may be independently controlled along each column (r) formed by the cell containment grooves 11 (hereinafter, a horizontal direction is referred to as a row and a vertical direction is referred to as a column, referring to FIG. 3).

The pressure control part 20 supports the cell containment part 10 and, at the same time, transforms the cell containment grooves 11 formed in the cell containment part 10 by applying pressure to the cell containment part 10.

More particularly, the pressure control part 20 may include a stage 21, a pump 22, and a control part 23. The stage 21 may include a plurality of the air holes 210 which support the cell containment part 10 and, at the same time, through which air can enter and exit. The air holes 210 may be formed in an upper part of the stage 21 and at a position corresponding to a bottom surface of the cell containment grooves 11. The pump 22 applies vacuum pressure to the cell containment part 10 by sucking air. More particularly, the pump 22 may vertically stretch the cells C contained in the cell containment grooves 11 by applying suction force to the bottom surface 13 of the cell containment part 10. Meanwhile, the control part 23 may control driving of the pump 22. The control part 23 may variously control an operation cycle of the pump 22 by adjusting a driving pressure and on/off frequency of the pump 22. The operation cycle of the pump 22 may be variously controlled to, for example, 1 Hz, 0.5 Hz, 2 Hz, or the like and may be differently controlled according to user's purpose.

The pressure control part 20 may include a plurality of air suction pipes 24. The air suction pipes 24 may be respectively disposed at positions corresponding to lower parts of the cell containment grooves 11 per row ($a_1$, $a_2$, $a_3$, $a_4$) formed by the cell containment grooves 11.

The air suction pipes 24 may include a first air suction pipe 241, a second air suction pipe 242, a third air suction pipe 243, and a fourth air suction pipe 244 which are respectively disposed at the rows ($a_1$, $a_2$, $a_3$, $a_4$) formed by the cell containment grooves 11.

The plurality of air suction pipes 241, 242, 243, and 244 may be respectively, independently controlled along the rows (a) or columns (r) formed by the cell containment grooves 11. Among the respective rows ($a_1$, $a_2$, $a_3$, $a_4$) formed by the cell containment grooves 11, bottom surfaces of the cell containment grooves 11 arranged in the same row are simultaneously stretched in a vertical direction when the pump 22 is driven and thus suction force occurs. That is, the cell containment grooves 11 constituting the same row may be identically transformed by vacuum pressure of the pump 22. Meanwhile, the respective rows ($a_1$, $a_2$, $a_3$, $a_4$) formed by the cell containment grooves 11 may be separately controlled in a column (r) direction. In other words, suction force of the pump 22 may be applied to some rows among the respective rows ($a_1$, $a_2$, $a_3$, $a_4$) or all of the respective rows. Accordingly, vacuum pressure may be selectively applied to a desired row.

The stage 21 may include a communication pipe 25 for communication between the air suction pipes 241, 242, 243, and 244. The communication pipe 25 may enable the plurality of air suction pipes 241, 242, 243, and 244, which are arranged at positions corresponding to the cell containment grooves 11, to communicate with each other in a column (r) direction. Here, the communication pipe 25 may include the valves 26 for controlling the flow of air such that air enters and exits only through the air suction pipe 24 disposed in a desired row among the rows ($a_1$, $a_2$, $a_3$, $a_4$) formed by the cell containment grooves 11.

The valves 26 may include a first valve 261, a second valve 262, a third valve 263, and a fourth valve 264 which selectively open and close paths between the respective air suction pipes 241, 242, 243, and 244 and the communication pipe 25.

For example, when all of the valves 26 are closed (see FIG. 5(a)), the cells C contained in the cell containment grooves 11 may be maintained in a state in which the cells C are attached to the bottom surface 13 of the cell containment part 10.

On the other hand, when all of the valves 26 are open and thus the respective air suction pipes 241, 242, 243, and 244 communicate with the communication pipe 25 (see FIG. 5(b)), the pump 22 is driven by the control part 23 such that air is sucked through the air suction pipes 241, 242, 243, and 244, whereby vacuum pressure is applied to the cell containment part 10. Accordingly, the bottom surface 13 of the cell containment part 10 is downwardly stretched and thus mechanical stimulation is applied to the cells C.

In addition, when only the first valve 261 among the valves 26 is opened and thus the first air suction pipe 241 communicates with the communication pipe 25 (see FIG. 5(c)), vacuum pressure may be applied only to the first row ($a_1$) formed by the cell containment grooves 11. Accordingly, the bottom surfaces 13 of the cell containment grooves 11 disposed in the first row ($a_1$) of the cell containment part 10 are downwardly stretched, whereby mechanical stimulation may be applied to the cells C.

Since the present disclosure adopts a manner wherein the bottom surface 13 of the cell containment part 10 is vertically, downwardly stretched by the pressure control part 20 and thus mechanical stimulation is applied to the cells C, the apparatus according to the present disclosure has superior spatial efficiency, compared to conventional apparatuses wherein mechanical stimulation is applied in a horizontal direction, and thus, has an advantage in that cells C may be cultured on a massive scale.

Figure 6A:
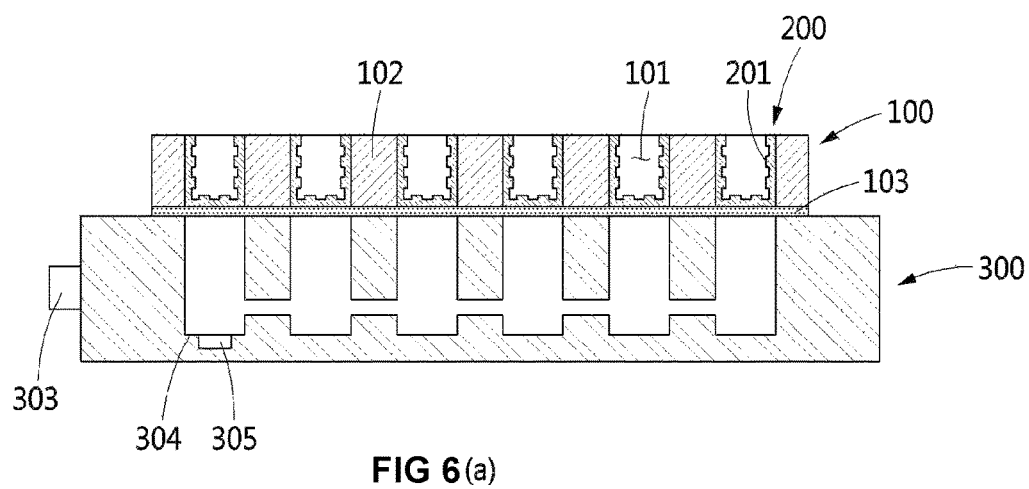
FIGS. 6(a) and 6(b) illustrate a sectional view of a cell stimulation apparatus according to another embodiment of the present disclosure.
Figure 6B:
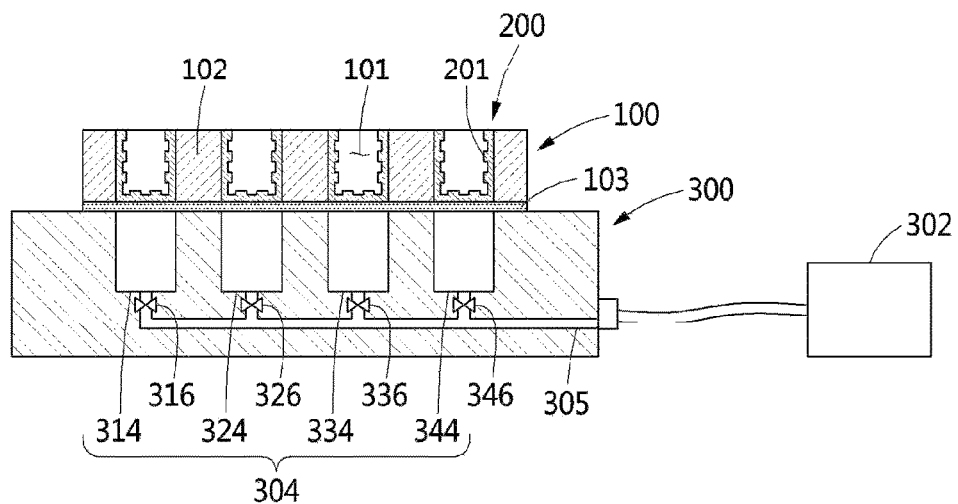

FIGS. 6(a) and 6(b) illustrate a sectional view of a cell stimulation apparatus according to another embodiment of the present disclosure.

Referring to FIG. 6, the cell stimulation apparatus according to another embodiment of the present disclosure may include a cell containment part 100 and a pressure control part 300, as in the cell stimulation apparatus 1 according to an embodiment of the present disclosure.

Meanwhile, a protrusion part 200 may be formed on inner circumferential surfaces 102 of the cell containment grooves 101 formed in the cell containment part 100 of the cell stimulation apparatus according to another embodiment of the present disclosure.

More particularly, the protrusion part 200 may be formed in a concave and convex shape 201 on inner circumferential surfaces 102 and a bottom surface 103 of the cell containment grooves 101. For example, although the protrusion part 200 is illustrated as having a concave and convex shape 201 in FIG. 6, the present disclosure is not limited thereto and the protrusion part 200 may have various shapes, such as a hemispherical shape or a triangular shape, to which the cells C may attach.

The protrusion part 200 may improve the adhesive property of the cells C contained in the cell containment grooves 101. In addition, since the protrusion part 200 is a part to which the contained cells C are attached, the protrusion part 200 is preferably made of a biocompatible material (e.g., polydimethylsiloxane, polyurethane).

The pressure control part 300 may include a pump 302 for applying vacuum pressure to the cell containment part 100 and a control part 303 for controlling the operation of the pump 302.

In addition, the pressure control part 300 may include a plurality of air suction pipes 304. More particularly, one air suction pipe 304 may be formed per row formed by the cell containment grooves 101. The cell containment grooves 101 may be arranged in a lattice shape on the cell containment part 100. Here, the air suction pipes 304 may include a first air suction pipe 314, a second air suction pipe 324, a third air suction pipe 334, and a fourth air suction pipe 344 which are disposed under each of the rows formed by the cell containment grooves 101.

A communication pipe 305 may be formed between the air suction pipes 314, 324, 334, and 344 such that the air suction pipes 314, 324, 334, and 344 communicate with each other along a column formed by the cell containment grooves 101. Here, the communication pipe 305 may include valves 316, 326, 336, and 346 for controlling the flow of air such that air enters and exits only through air suction pipes 304 at a desired row among the plurality of rows formed by the cell containment grooves 101.

The valves may include a first valve 316, a second valve 326, a third valve 336, and a fourth valve 346 which selectively open and close paths between the respective air suction pipes 314, 324, 334, and 344 and the communication pipe 305. The flow of air between each of the air suction pipes 304 and the communication pipe 305 is controlled by partially or entirely opening or closing each of the valves 316, 326, 336, and 346, whereby the cell containment grooves 101 disposed at a desired row may be transformed.

Figure 7:
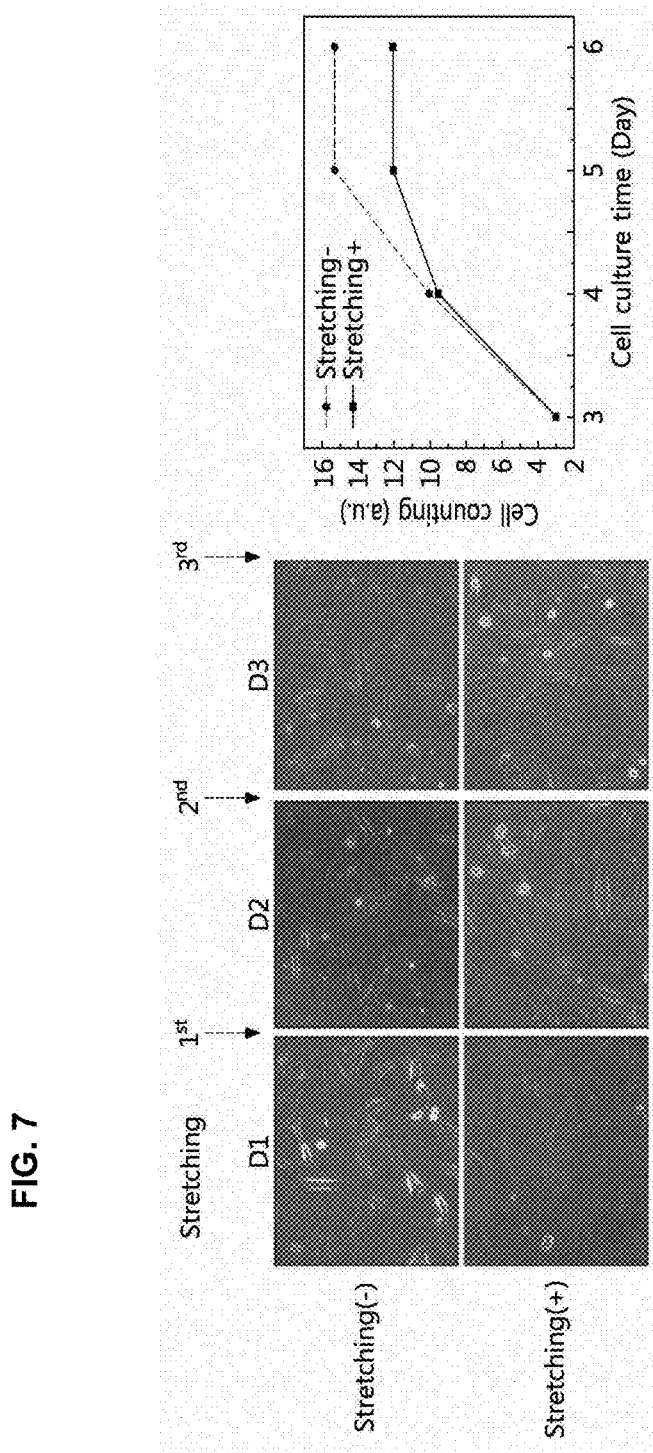
FIGS. 7 and 8 illustrate results of human dermal fibroblast growth promotion experiments using a cell stimulation apparatus according to an embodiment of the present disclosure.
Figure 8:
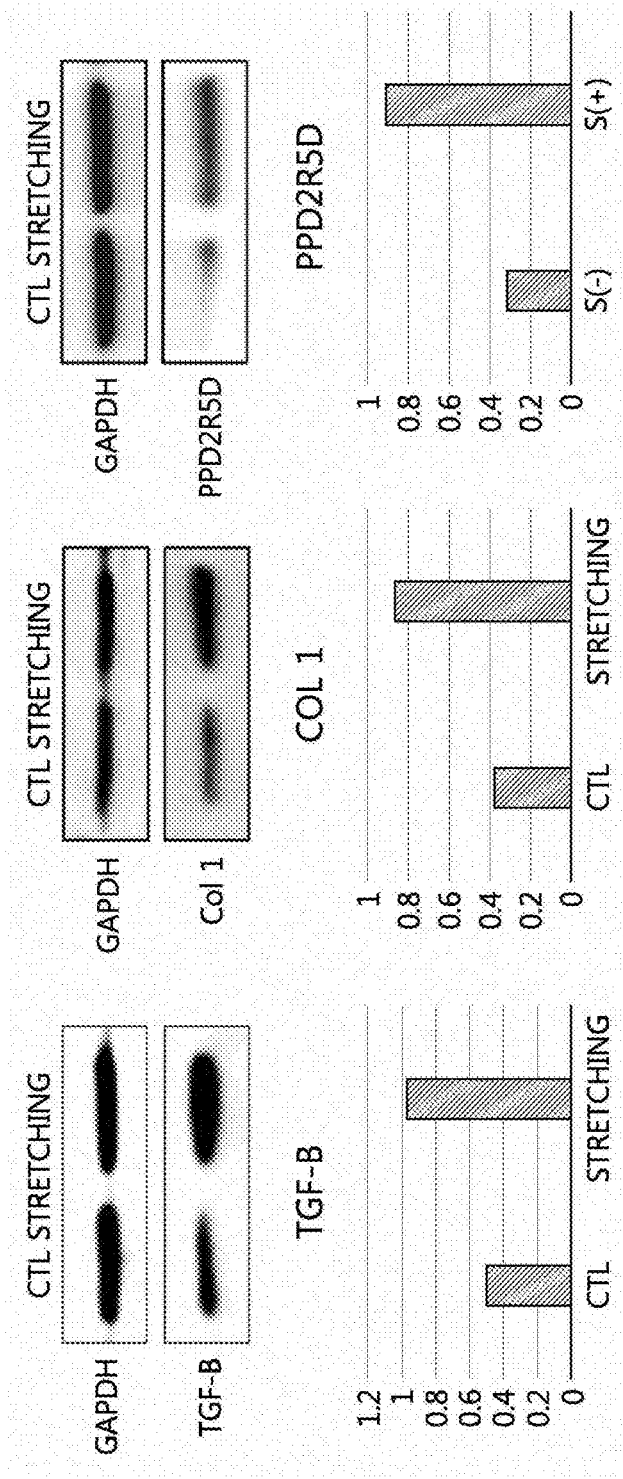

FIGS. 7 and 8 illustrate results of human dermal fibroblast growth promotion experiments using a cell stimulation apparatus according to an embodiment of the present disclosure.

Referring to FIGS. 7 and 8, results of human dermal fibroblast growth promotion experiments by means of the cell stimulation apparatus 1 according to an embodiment of the present disclosure can be confirmed.

As the human dermal fibroblast growth promotion experiment results, it can be confirmed that the growth of human dermal fibroblasts is increased 1.2 times during the same period when mechanical stimulation (vacuum pressure) is applied to the human dermal fibroblasts, and the cells grow in a direction in which the mechanical stimulation is applied (see FIG. 7).

In addition, as results of analyzing protein expression differences in cells by human dermal fibroblast growth promotion experiments, it can be confirmed that, in cells cultured while being mechanically stimulated by means of the cell stimulation apparatus 1 according to an embodiment of the present disclosure, the expression levels of the growth promotion factor (TGF-B), collagen, and cell proliferative factor (PPP2R5D) are increased by 2×, 2.3×, and 2.9× or more, respectively (see FIG. 8).

Hereinafter, the operation of the cell stimulation apparatus according to an embodiment of the present disclosure is described.

The cell stimulation apparatus 1 may culture the cells C while applying mechanical stimulation to the cells C using vacuum pressure. In other words, by applying tensile force to the cells C, growth of the cells C may be promoted and functional aspects of the cells C may be improved.

For example, by applying tensile force to the cells C, growth of the cells C may be promoted such that a conventional growth period, i.e., three days, of the cells C is reduced to one day.

In addition, by applying tensile force to stem cells among the cells C, which are differentiated into various cell types such as bone, skin, or nerve cells, a differentiation path of the stem cells may be determined. Furthermore, proteins expressed in such stem cells may be used as drugs.

Further, the amounts of proteins expressed in the cells C increase by applying tensile force to the cells C, whereby functional aspects of the cells C may be improved. Similar to FIG. 8, when skin cells are cultured while applying tensile force, the amount of collagen protein expressed in the skin cells may be increased.

As apparent from the above description, since the bottom of the cell containment part of the apparatus according to the present disclosure is stretched in a vertical direction to apply mechanical stimulation, the apparatus according to the present disclosure provides superior spatial efficiency and thus facilitates mass cell culture.

In addition, since the apparatus according to the present disclosure uses suction force of the pump, conventional problems, such as wear and damage caused due to repeated movements of a machine to provide stimuli to cells, may be prevented.

In addition, by applying mechanical stimulation to cells according to the present disclosure, the growth of the cells may be promoted, a differentiation path of the cells may be determined, and the functional aspects of the cells may be improved by increasing the amounts of proteins expressed in the cells.

Further, the cell stimulation apparatus according to the present disclosure may be applied to various fields such as experimental, research, industrial fields.

What is claimed is:

1. A cell stimulation apparatus, comprising:
   a cell containment part in which a plurality of cell containment grooves containing cells are formed; and
   a pressure control part that supports the cell containment part and transforms the plurality of cell containment grooves by applying pressure to the cell containment part,
   wherein a bottom of the cell containment part is made of a flexible material,
   wherein a plurality of protrusions are formed in the plurality of cell containment grooves,
   wherein the pressure control part comprises:
   a stage which supports the cell containment part and includes air holes through which air enters and exits;
   a pump that applies vacuum pressure to the cell containment part in a vertical direction; and
   a control part that controls driving of the pump,
   wherein a plurality of air suction pipes are provided to the stage, wherein the plurality of air suction pipes are disposed at positions corresponding to the plurality of cell containment grooves, and wherein air suction pipes among the plurality of air suction pipes disposed in a same row or a same column of a plurality of rows and columns formed by the plurality of cell containment grooves are controlled independently from the other air suction pipes among the plurality of air suction pipes.

2. The cell stimulation apparatus according to claim 1, wherein the bottom of the cell containment part is made of a stretchable polymer material.

3. The cell stimulation apparatus according to claim 1, wherein the plurality of cell containment grooves are formed in a lattice shape in the plurality of rows and columns on the cell containment part, and the pressure control part independently controls pressure applied to each of the plurality of cell containment grooves.

4. The cell stimulation apparatus according to claim 1, wherein the holes are formed at an upper part of the stage and correspond to the plurality of cell containment grooves.

5. The cell stimulation apparatus according to claim 1, wherein cell containment grooves included in an identical row among rows formed by the plurality of cell containment grooves are stretched together, and each row formed by cell containment grooves of the plurality of cell containment grooves is separately controlled, the stage comprises a communication pipe communicating between the air suction pipes, and the communication pipe comprises valves for controlling entry and exit of air which is sucked through the air suction pipes by driving of the pump.

6. The cell stimulation apparatus according to claim 5, wherein the valves control flow of air such that air is sucked only through air suction pipes disposed at a desired row among the air suction pipes.

7. A cell stimulation apparatus, comprising:

a cell containment part in which a plurality of cell containment grooves containing cells are formed;

a protrusion part that is formed, in a concave and convex shape, on inner circumferential surfaces of the plurality of cell containment grooves; and a pressure control part that supports the cell containment part and controls intensity of mechanical stimulation applied to cells by applying pressure to the cell containment part, wherein a bottom of the cell containment part is made of a flexible material, wherein the pressure control part comprises:

a stage which supports the cell containment part and includes air holes through which air enters and exits;

a pump that applies vacuum pressure to the cell containment part in a vertical direction; and a control part that controls driving of the pump, wherein a plurality of air suction pipes are provided to the stage, wherein the plurality of air suction pipes are disposed at positions corresponding to the plurality of cell containment grooves, and wherein air suction pipes among the plurality of air suction pipes disposed in a same row or a same column of plurality of rows and columns formed b the plurality of cell containment grooves are independently controlled from the other air suction pipes of the plurality of air suction pipes.

8. The cell stimulation apparatus according to claim 7, wherein the bottom and the protrusion part are made of a stretchable polymer material.

9. The cell stimulation apparatus according to claim 7, wherein cell containment grooves included in an identical row among rows formed by the plurality of cell containment grooves are stretched together, and each row formed by cell containment grooves of the plurality of cell containment grooves is separately controlled, the stage comprises a communication pipe communicating between the air suction pipes that are disposed per row formed by the cell containment grooves, and the communication pipe comprises valves for controlling entry and exit of air which is sucked through the air suction pipes by driving of the pump.

10. The cell stimulation apparatus according to claim 9, wherein the valves control flow of air such that air is sucked only through air suction pipes disposed at a desired row among the air suction pipes.

* * * * *